US00PP15260P3

(12) United States Plant Patent
Warren et al.

(10) Patent No.: US PP15,260 P2
(45) Date of Patent: Oct. 19, 2004

(54) CALLA LILY PLANT NAMED 'HOT LIPS'

(50) Latin Name: *Zantedeschia*
Varietal Denomination: Hot Lips

(75) Inventors: Andrew G. F. Warren, Tauranga (NZ); Jacobus J. P. Spaans, Tauranga (NZ)

(73) Assignee: Bloomz Ltd. (NZ)

( * ) Notice: Subject to any disclaimer, the term of this patent is extended or adjusted under 35 U.S.C. 154(b) by 0 days.

(21) Appl. No.: 10/382,810

(22) Filed: Mar. 6, 2003

(65) Prior Publication Data

US 2004/0177422 P1 Sep. 9, 2004

(51) Int. Cl.[7] ..... A01H 5/00

(52) U.S. Cl. ..... Plt./263

(58) Field of Search ..... Plt./263

(56) References Cited

PUBLICATIONS

UPOV–ROM GTITM Computer Database, 2003/04, GTI Jouve Retrieval Software, citation for 'Hot Lips'.*

* cited by examiner

*Primary Examiner*—Kent Bell
*Assistant Examiner*—Susan B. McCormick-Ewoldt
(74) *Attorney, Agent, or Firm*—Jondle & Associates P.C.

(57) ABSTRACT

A calla lily plant particularly distinguished by dark pink spathe and maculated leaves.

4 Drawing Sheets

Genus and species: *Zantedeschia* species.
Variety denomination: 'Hot Lips'.

BACKGROUND OF THE NEW PLANT

The present invention comprises a new and distinct cultivar of calla lily, botanically known as *Zantedeschia* spp, and hereinafter referred to by the cultivar name 'Hot Lips'. The new cultivar is asexually reproduced from vegetative cuttings and tissue culture resulting from the cross of the seed parent 'Pink Persuasion' (patent status unknown)× pollen parent 'Majestic Red' (patent status unknown).

'Hot Lips' is a product of a planned breeding program intended to create new calla lily plants with dark pink spathes.

The new cultivar was created in 1998 in Tauranga New Zealand and has been asexually reproduced repeatedly by vegetative cuttings and tissue culture in New Zealand over a 3 year period. The present invention has been found to retain its distinctive characteristics through successive propagations; and this novelty is firmly fixed.

DESCRIPTION OF PHOTOGRAPH

This new calla lily plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
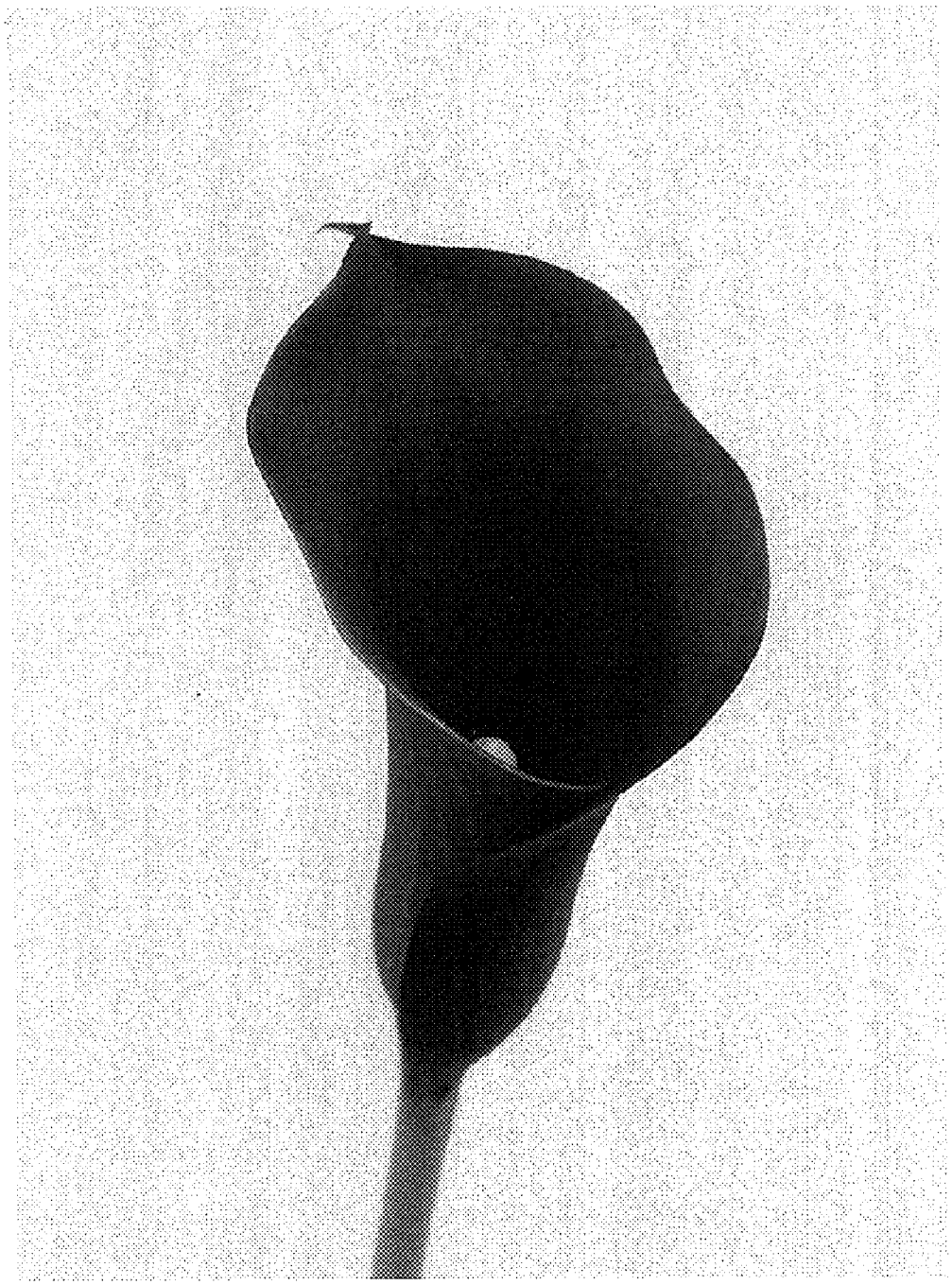
FIG. 1 shows the mature inflorescence.
Figure 2:
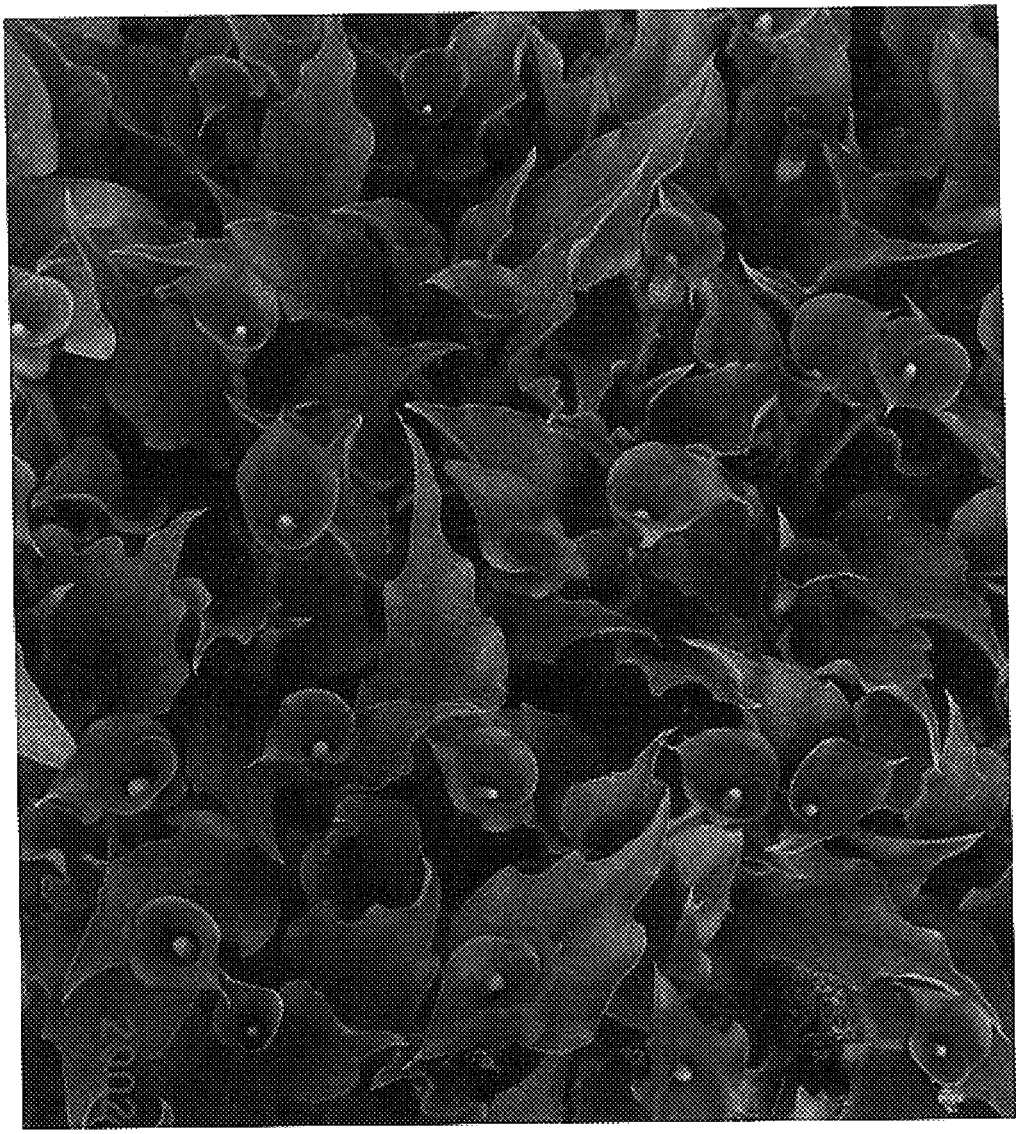
FIG. 2 shows the overall plant habit.
Figure 3:
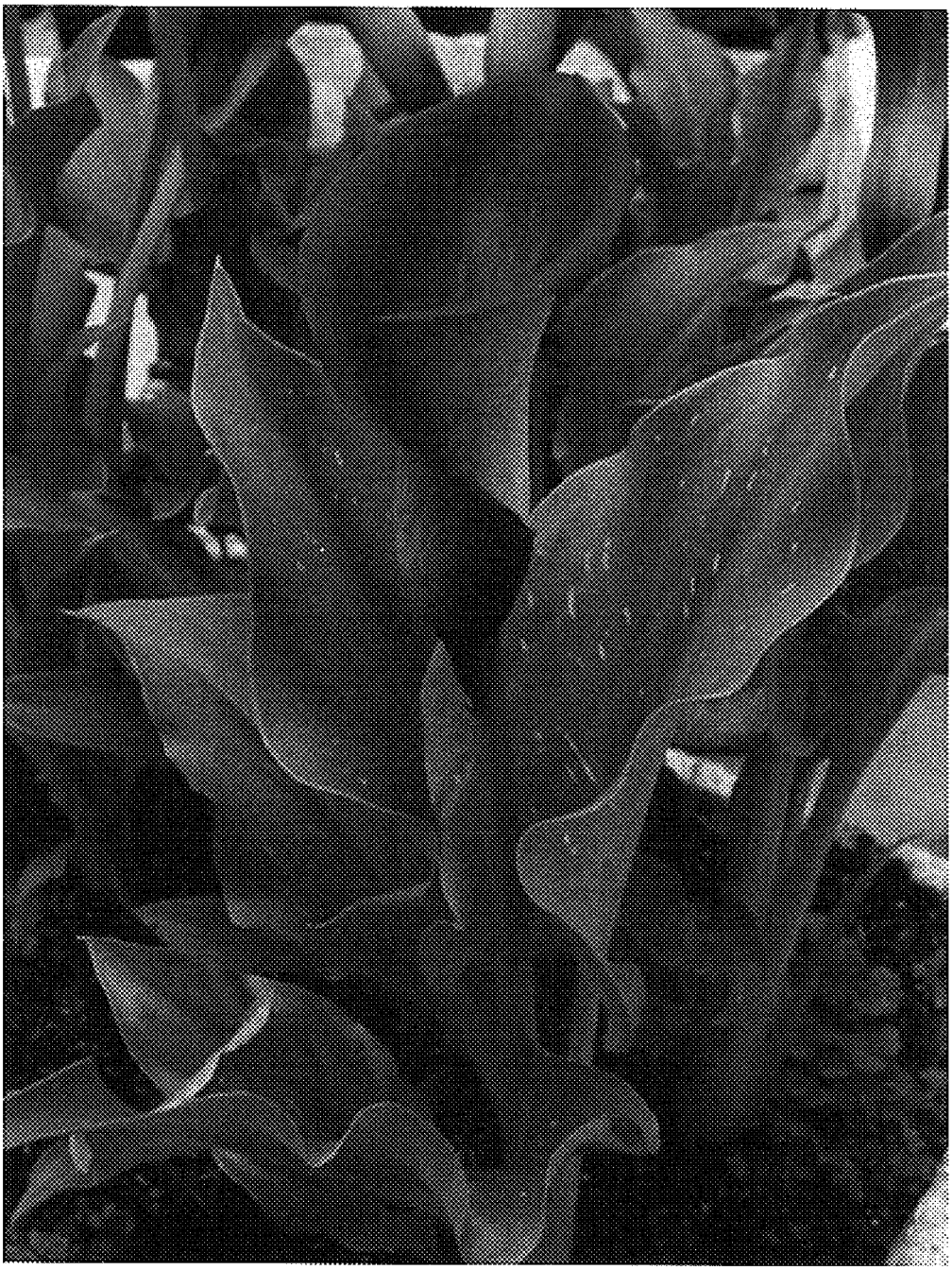
FIG. 3 shows the inflorescence and leaves.
Figure 4:
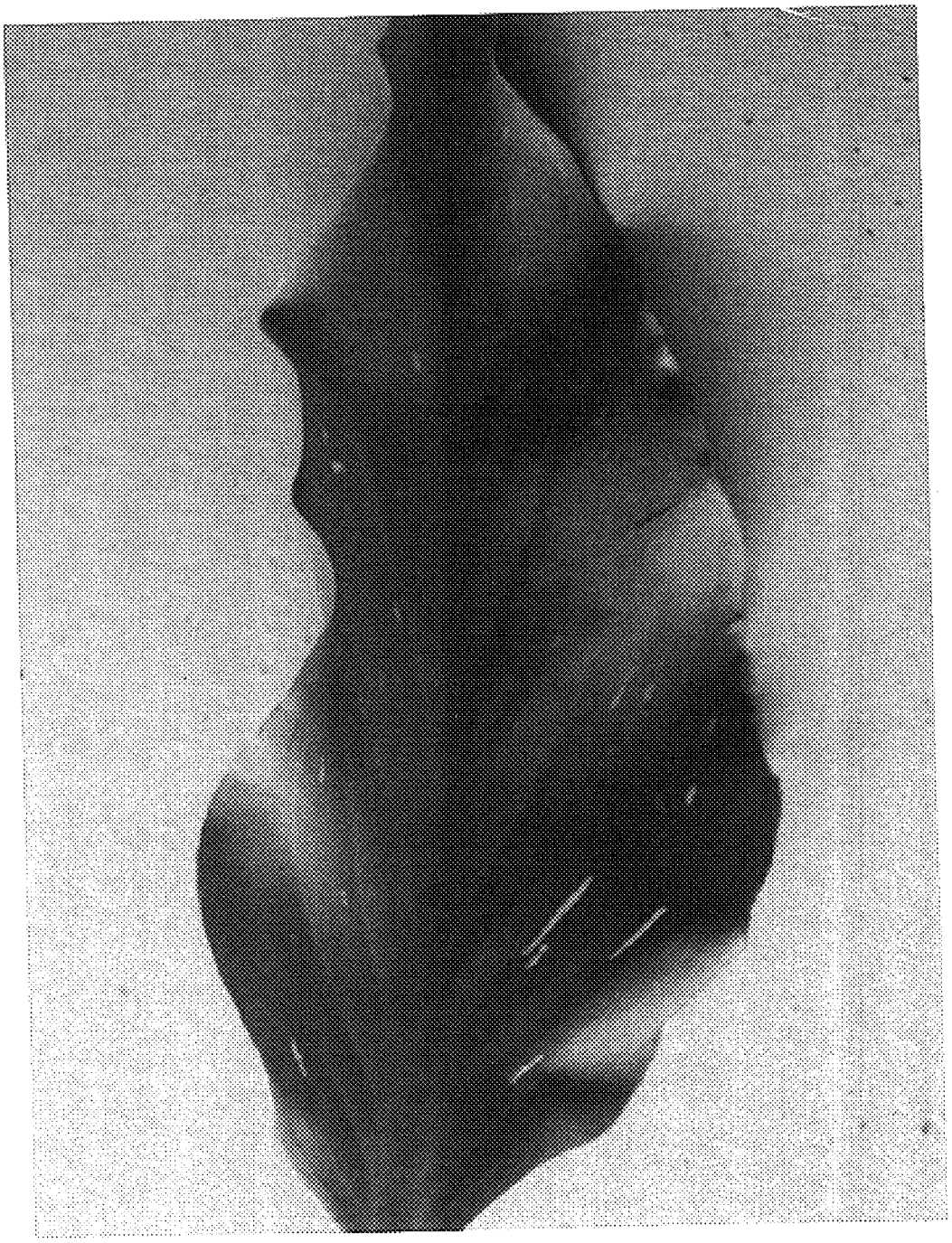
FIG. 4 shows a close-up of the leaf.

The following detailed descriptions set forth the distinctive characteristics of 'Hot Lips'. The data which defines these characteristics were collected from asexual reproductions carried out in New Zealand. The plant history was taken on 2 year old plants based on a 4 cm diameter tuber under New Zealand Spring conditions. Color references are primarily to The RHS Colour Chart of The Royal Horticultural Society of London (RHS).

THE PLANT

Classification:
- *Botanical.*—*Zantedeschia* spp.
- *Commercial.*—Calla lily.
- *Variety.*—'Hot Lips'.

Size:
- *Form.*—Erect.
- *Height of the leaf canopy above the soil.*—45–55 cm.
- *Height of top of inflorescence above the soil.*—60–75 cm.
- *Diameter.*—30–40 cm.
- *Number of inflorescence per tuber size.*—Tuber diameter 3 cm 2–4. Tuber diameter 4 cm 4–7. Tuber diameter 5 cm 7+.

Branches:
- *Character.*—Strong.
- *Color.*—Upper is green RHS 144A; lower is green RHS 145A; base is white RHS 155B.
- *Average number.*—2–3.

Leaves:
- *Size.*—Width 10–15 cm; length 25–30 cm.
- *Shape.*—Ovate.
- *Color.*—Upper is green RHS 137B; lower is green RHS 137C.
- *Maculation* (*leaf spots*).—Low density; white RHS 155C.
- *Apex.*—Acute to apiculate.
- *Margin.*—Moderately wavy.
- *Margin color.*—Yellow-Green RHS 145A.
- *Veins.*—Pinnate.
- *Surface quality.*—Leathery.

Petiole (leaf stalk):
*Length.*—40–50 cm.
*Color.*—Base is green RHS 144C; upper is green RHS 144B.
Roots:
*Color.*—White.
*Branching.*—Not branched, attached to the top of the tuber at the apices.
*Disease resistance.*—No susceptibility noted to date.
*Pest resistance.*—No susceptibility noted to date.

THE INFLORESCENCE

Spathe (flower body):
*Size.*—Length 8–10 cm; width 4–6 cm.
*Color.*—Upper is pink red RHS 60B; lower is pink red RHS 60C.
*Veins.*—Present, red purple RHS 51A.
*Shape.*—Fluted.
Spadix (reproductive organs):
*Size.*—Length 3.5–4 cm; diameter 0.6–1.0 cm.
*Color.*—Base is yellow RHS 10C; Upper is yellow RHS 10B.
*Position relative to spathe.*—Upright.
Peduncle (flower stem):
*Size.*—50–60 cm.
*Color.*—Green RHS 145A; upper is Green RHS 145B.
Reproductive organs:
*Location of female organs.*—Basal position of the spadix.
*Location of male organs.*—Upper position of the spadix Perianth (the floral envelope — calyx and corolla) Conspicuous.
*Stamens.*—Not visible before pollen release.
*Pistil.*—30–40 per spadix; yellow RHS 10B.
Miscellaneous:
*Time to produce a finished flowering plant.*—6–10 weeks.
*Lastingness.*—2–3 weeks.
*Fragrance.*—None.
*Fruit production.*—30–40 berries.
*Color.*—Predominantly green RHS 150C.

COMPARISON WITH KNOWN CULTIVARS

When the instant plant is compared to 'Pink Persuation' (patent status unknown) the 'Hot Lips' foliage has a low density of maculation and the color of the leaves is darker green. Additionally the spathe color is more intense than 'Pink Persuation'. 'Hot Lips' is distinguished from 'Majestic Red' primarily in spathe color.

I claim:

1. A new and distinct cultivar of calla lily plant as shown and described herein.

* * * * *